U.S. Patent Number: 5,462,970
Date of Patent: Oct. 31, 1995

United States Patent [19]
Bergeron, Jr. et al.

[54] POLYAMINES AND ANTI-DIARRHEAL AND GASTROINTESTINAL ANTI-SPASMODIC PHARMACEUTICAL COMPOSITIONS AND METHODS OF TREATMENT

[75] Inventors: Raymond J. Bergeron, Jr.; Charles A. Sninsky, both of Gainesville, Fla.

[73] Assignee: University of Florida Research Foundation, Inc., Gainesville, Fla.

[21] Appl. No.: 367,862

[22] Filed: Jan. 3, 1995

Related U.S. Application Data

[60] Division of Ser. No. 61,707, May 17, 1993, Pat. No. 5,393,757, which is a continuation-in-part of Ser. No. 870,441, Oct. 9, 1991, abandoned, which is a continuation-in-part of Ser. No. 210,520, Jun. 23, 1988, Pat. No. 5,091,576, which is a continuation-in-part of Ser. No. 66,227, Jun. 25, 1987, abandoned, which is a continuation-in-part of Ser. No. 936,835, Dec. 2, 1986, abandoned.

[51] Int. Cl.$^6$ ............... A61K 31/135; A61K 31/13
[52] U.S. Cl. ............... 514/654; 514/655; 514/674; 564/367; 564/512
[58] Field of Search ............... 514/654, 655, 514/674; 564/367, 512

[56] References Cited

U.S. PATENT DOCUMENTS

| | | | |
|---|---|---|---|
| 2,267,204 | 12/1941 | Kgrides | 514/674 |
| 4,321,190 | 3/1982 | Costanzi et al. | 524/252 |
| 4,507,321 | 3/1985 | Raisfeld | 514/673 |
| 4,591,605 | 5/1986 | Ray | 514/579 |
| 5,091,576 | 2/1992 | Bergeron | 564/367 |
| 5,109,024 | 4/1992 | Prakash et al. | 514/674 |
| 5,242,947 | 9/1973 | Cherksey et al. | 514/628 |
| 5,342,945 | 8/1994 | Bergeron | 544/296 |
| 5,393,757 | 2/1995 | Bergeron | 514/256 |

OTHER PUBLICATIONS

Weinstock et al, "Synthesis of New Polyamine Derivatives for Cancer Chemotherapeutic Studies", Journal of Pharm. Sciences, vol. 70, No. 8, (1981).

Chantrapromma et al, "Chemistry of Naturally Occuring Polyamines", Tetrahedron Lett., vol. 22(1), 23–24, (1981).

Tansy et al, "Spermine and Spermidine as Inhibitors of Gastro Intestinal Motor Activity", Surg. Gynecol. Obstec., 154 (1), 74–80, (1982).

Aihara et al, "Polyamine Inhibition of Gastric Ulceration and Secretion in Rats", Biochem. Pharmacol., vol. 32(11), 1733–1736, (1983).

Ray et al, "Polyamines are Inhibitors of Gastric acid Secretion", Proc. Natl. Acad. Sci. USA, vol. 79 (5), 1448–1452, (1982).

*Primary Examiner*—Richard L. Raymond
*Assistant Examiner*—Deborah Lambkin
*Attorney, Agent, or Firm*—Kerkam, Stowell, Kondracki & Clarke; Dennis P. Clarke

[57] ABSTRACT

Anti-diarrheal, anti-secretory, nitric oxide agonist, nitric oxide synthase activating or gastrointestinal anti-spasmodic compounds of the formula:

$$R_1-N^1-(CH_2)_m-N^2-(CH_2)_n-N^3-(CH_2)_m-N^4-R_6; \quad (I)$$
$$\phantom{R_1-N^1}\ \ |\phantom{-(CH_2)_m-}\ \ |\phantom{-(CH_2)_n-}\ \ |\phantom{-(CH_2)_m-}\ \ |$$
$$\phantom{R_1-N^1-(CH_2)_m-}R_2\phantom{-(CH_2)_n-}R_3\phantom{-(CH_2)_m-}R_4\phantom{-(CH_2)_m-}R_5$$

$$R_1-N^1H-(CH_2)_3-N^2H-(CH_2)_3-N^3H-(CH_2)_4-N^4H- \quad (II)$$
$$-(CH_2)_3-N^5H-(CH_2)_3-N^6H-R_6;$$

or (III) a cyclic structure with $R_1$, $R_6$ on $N^1$, $N^4$, linked via $R_7$ groups and $N^2-(CH_2)_n-N^3$.

wherein:

$R_1$ and $R_6$ may be the same or different and are H, alkyl or aralkyl having from 1 to 12 carbon atoms;

$R_2$–$R_5$ may be the same or different and are H, $R_1$ or $R_6$;

$R_7$ is H, alkyl, aryl or aralkyl having from 1 to 12 carbon atoms;

m is an integer from 3 to 6, inclusive; and
n is an integer from 3 to 6, inclusive; or (IV) a salt thereof with a pharmaceutically acceptable acid; and a pharmaceutically acceptable carrier therefor. Methods of treatment utilizing the composition are also disclosed.

10 Claims, No Drawings

POLYAMINES AND ANTI-DIARRHEAL AND GASTROINTESTINAL ANTI-SPASMODIC PHARMACEUTICAL COMPOSITIONS AND METHODS OF TREATMENT

This invention was made with United States Government support under Grant NCDDG-CA37606, awarded by the National Cancer Institute. The United States Government has certain rights in this invention.

RELATED APPLICATIONS

This is a division of application Ser. No. 08/061,707 filed May 17, 1993, now U.S. Pat. No. 5,393,757 which is a continuation-in-part of application Ser. No. 07/870,441 filed Oct. 9, 1991, now abandoned which is a continuation-in-part of application Ser. No. 07/210,520 filed Jun. 23, 1988, now U.S. Pat. No. 5,091,576, which is a continuation-in-part of application Ser. No. 07/066,227 filed Jun. 25, 1987, now abandoned, which was a continuation-in-part of application Ser. No. 06/936,835 filed Dec. 2, 1986, now abandoned.

BACKGROUND OF THE INVENTION

The present invention relates to certain novel anti-diarrheal and gastrointestinal anti-spasmodic agents and methods of treatment and pharmaceutical compositions based thereon.

DESCRIPTION OF THE PRIOR ART

Diarrhea can result from a variety of pathophysiological disorders including bacterial and parasitic infections, disease or debilitation of organs such as liver, adrenal and others. It can also occur as a result of other therapy or diet. In all cases, diarrhea is generally a symptom of organic gastrointestinal disorders and not itself a disorder. Chronic diarrhea is generally due to: (1) hypersecretion of fluid and electrolytes of the stomach, small intestine and colon; (2) inability to absorb certain nutrients (malabsorption); and (3) intestinal hypermotility and rapid transport. These may occur separately or in combination. Certain disorders may have diarrhea as a prominent feature of the disease/syndrome, but the specific etiology is unclear. In this latter group, emotional tension and psychological factors may adversely influence the frequency of the symptoms.

Diarrhea and diarrheal diseases are one of the most frequent causes of morbidity and mortality, especially in less developed countries wherein the number of those killed by such diseases is estimated at about 5 million persons per annum. Particularly dangerous are diarrheal diseases of the newborn and the youngest group of babies (S. Hughes: Drugs, Vol. 26, pp. 80–90 (1983)).

In mechanized or automated large capacity farms, diarrhea and infections of the respiratory tract are frequent, especially with young livestock and the high mortality or growth deceleration thereof have a considerable negative economical effect. Diarrheal diseases of man and animals are caused by a plurality of etiological factors, especially of microbial and viral character. The most prevalent microbes are gram-negative bacteria, *Escherichia coli* and *Vibrio cholerae*. However, it is now clear that other bacteria, viruses and parasites (protozoan, amoeba, etc.) also cause severe problems.

Diarrheal diseases are treated by rehydration therapy using preparations composed of various salts (potassium chloride, sodium chloride, sodium hydrogen carbonate) and glucose, whereby quick compensation for the loss of water and ions, as well as for acidosis, occurs. However, the occurrence of diarrheal diseases is not influenced. Other substances of the same kind produce similar results.

Anti-diarrheal compounds are, of course, well known in the medicinal arts and take various forms. In particular, there are a variety of products known which act systemically to provide anti-diarrheal effects when administered in a manner which will enable the drug to be taken into the system at effective therapeutic levels.

In addition, there are anti-cholinergic substances applied together with spasmolytics such as Reasec® (Janssen) which contain diphenyloxylate and atropin. Both human and veterinary medicine use chemotherapeutic agents with anti-bacterial effects, such as sulfonamides, or antibiotics are availed of which are apt to suppress certain infections.

Medicaments are also aimed at the sphere of regulation depending on receptors, especially those localized on the basolateral membrane, further by means of an intracellular mechanism of intervention by the so-called secondary messenger, and by influencing the transport mechanism, especially boundary membranes. The modulation of receptor-dependent regulation mechanisms can be influenced, to some extent, by medicaments of the type alpha$_2$ adrenergic agonists such as clonidine (Catapresan®) (E. B. Chang et al, Gastroenterology, Vol. 91, pp. 564–569 (1986)), somatostatin, or encephalin and morphine analogs. For influencing the transport of ions through the membrane, it is also possible to use alpha$_2$ adrenergic agonists (E. B. Chang et al, Am. J. Physiol., Vol. 1982, p. 242). Reference has also been made to the use of lidamidine, i.e., the medicament having a damping effect on the intestine peristaltics (M. D. Dharmsathphorn: Gastroenterology, Vol. 91, pp. 769–775 (1986)).

Disadvantages of anti-diarrheal medicaments, i.e., those referred to in professional papers rather than those medicaments of this type applied in practice, include their secondary strong effects such as anti-hypertensive effects (clonidine), growth factors (somatostatin), habituation and/or incomplete pre-clinical research (encephalin derivatives). The application of large doses of antibiotics and long administration thereof has not proved optimum in epidemical diarrhea localities. Where the diarrhea inducing agent is cholera toxin, however, there does not exist any efficient protection, except for inoculum which is not sufficiently patent either, and gives short term protection only (3 months) and low efficiency (30–40%).

In recent years, a great deal of attention has been focussed on the polyamines, e.g., spermidine, norspermidine, homospermidine, 1,4-diaminobutane (putrescine) and spermine. These studies have been largely directed at the biological properties of the polyamines probably because of the role they play in proliferative processes. It was shown early on that the polyamine levels in dividing cells, e.g., cancer cells, are much higher than in resting cells. See Janne et al, A. Biochim. Biophys. Acta., Vol. 473, p. 241 (1978); Fillingame et al, Proc. Natl. Acad. Sci. U.S.A., Vol. 72, p. 4042 (1975); Metcalf et al, J. Am. Chem. Soc., Vol. 100, p. 2551 (1978); Flink et al, Nature (London), Vol. 253, p. 62 (1975); and Pegg et al, Polyamine Metabolism and Function, Am. J. Cell. Physiol., Vol. 243, pp. 212–221 (1982).

Several lines of evidence indicate that polyamines, particularly spermidine, are required for cell proliferation: (i) they are found in greater amounts in growing than in non-growing tissues; (ii) prokaryotic and eukaryotic mutants deficient in polyamine biosynthesis are auxotrophic for polyamines; and (iii) inhibitors specific for polyamine biosynthesis also inhibit cell growth. Despite this evidence, the precise biological role of polyamines in cell proliferation is uncertain. It has been suggested that polyamines, by virtue of their charged nature under physiological conditions and their conformational flexibility, might serve to stabilize macromolecules such as nucleic acids by anion neutralization. See Dkystra et al, Science, Vol. 149, p. 48 (1965); Russell et al, Polyamines as Biochemical Markers of Normal and Malignant Growth (Raven, New York, 1978); Hirschfield et al, J. Bacteriol., Vol. 101, p. 725 (1970); Hafner et al, J. Biol. Chem., Vol. 254, p. 12419 (1979); Cohn et al, J. Bacteriol., Vol. 134, p. 208 (1978); Pohjatipelto et al, Nature (London), Vol. 293, p. 475 (1981); Mamont et al, Biochem. Biophys. Res. Commun., Vol. 81, p. 58 (1978); Bloomfield et al, Polyamines in Biology and Medicine (D. R. Morris and L. J. Morton, eds., Dekker, New York, 1981), pp. 183–205; Gosule et al, Nature, Vol. 259, p. 333 (1976); Gabbay et al, Ann. N. Y. Acad. Sci., Vol. 171, p. 810 (1970); Suwalsky et al, J. Mol. Biol., Vol. 42, p. 363 (1969); and Liquori et al, J. Mol. Biol., Vol. 24, p. 113 (1968).

However, regardless of the reason for increased polyamine levels, the phenomenon can be and has been exploited in chemotherapy. See Sjoerdsma et al, Butterworths Int. Med. Rev.: Clin. Pharmacol. Thera., Vol. 35, p. 287 (1984); Israel et al, J. Med. Chem., Vol. 16, p. 1 (1973); Morris et al, Polyamines in Biology and Medicine; Dekker, New York, p. 223 (1981); and Wang et al, Biochem. Biophys. Res. Commun., Vol. 94, p. 85 (1980).

It has been previously reported that diethylhomospermine (DEHSPM) inhibited myoelectric activity and transit of the small intestine in rats [J. Gastro. Motil., Vol. 1, p. 53 (1989)]. This inhibition was reversed with co-administration of bethanechol, a cholinergic agonist, but not with other agonists or antagonists [Gastro., Vol. 98, p. A388 (1990)]. However, there is no suggestion or disclosure in the prior art that any of the above-described polyamines have utility as anti-diarrheal or gastrointestinal anti-spasmodic agents.

It is an object of the present invention to provide novel anti-diarrheal and gastrointestinal anti-spasmodic pharmaceutical compositions containing certain polyamine compounds which are not subject to the above-noted disadvantages associated with prior art agents.

SUMMARY OF THE INVENTION

The foregoing and other objects are realized by the present invention, one embodiment of which is an anti-diarrheal, anti-secretory, nitric oxide agonist, nitric oxide synthase activating or gastrointestinal anti-spasmodic pharmaceutical composition comprising an anti-diarrheal or gastrointestinal anti-spasmodic (hereinafter "GI anti-spasmodic") effective amount of a compound of the formulae set forth below and a pharmaceutically acceptable carrier therefor.

An additional embodiment of the present invention comprises a method of treating a human or non-human animal in need thereof comprising administering to the animal an anti-diarrheal or GI anti-spasmodic effective amount of a compound of the formulae below.

Suitable polyamines for use in the composition and method of the invention are those described in application Ser. No. 07/210,520 filed Jun. 23, 1988, now U.S. Pat. No. 5,091,576.

The polyamines suitable in the practice of the invention include those having the formula:

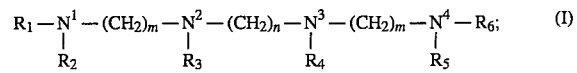

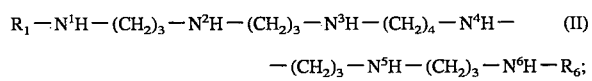

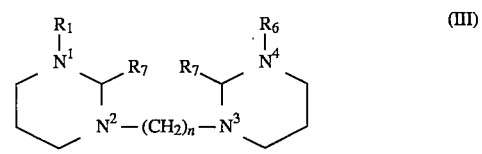

wherein:

$R_1$ and $R_6$ may be the same or different and are H, alkyl or aralkyl having from 1 to 12 carbon atoms;

$R_2$–$R_5$ may be the same or different and are H, $R_1$ or R6;

$R_7$ is H, alkyl, aryl or aralkyl having from 1 to 12 carbon atoms;

m is an integer from 3 to 6, inclusive; and n is an integer from 3 to 6, inclusive; or (IV) a salt thereof with a pharmaceutically acceptable acid;

and a pharmaceutically acceptable carrier therefor.

DETAILED DESCRIPTION OF THE INVENTION

The present invention is predicated on the discovery that polyamines of the above formulae act to inhibit the potential for the large and small intestines to contract. While not wishing to be bound by any theory as to the mechanism of action of the polyamines as inhibitors of this action of the intestines, it is hypothesized that the polyamines function via a receptor-dependent regulation mechanism whereby the myoelectric activity of the muscle tissue of the colon and small intestine and the secretion of fluid and electrolytes by these organs are modulated. In addition, some of these above effects may be directly or indirectly mediated through the release of nitric oxide or through the activation of nitric oxide synthase.

For each of the utilities mentioned herein, the amount required of active agent, the frequency and mode of its administration will vary with the identity of the agent concerned and with the nature and severity of the condition being treated and is, of course, ultimately at the discretion of the responsible physician or veterinarian. In general, however, a suitable dose of agent will lie in the range of about 0,001 mg to about 500 mg per kilogram of mammal body weight being treated. Administration by the parenteral route (intravenously, intradermally, intraperitoneally, intramuscularly or subcutaneously) is preferred for a period of time of from one to ten days. For chronic problems, the drug is administered as needed.

While it is possible for the agents to be administered as the raw substances, it is preferable, in view of their potency, to present them as a pharmaceutical formulation. The formulations of the present invention, both for veterinary and human use, comprise the agent together with one or more acceptable carriers therefor and optionally other therapeutic ingredients. The carrier(s) must be "acceptable" in the sense of being compatible with the other ingredients of the formulation and not deleterious to the recipient thereof. Desirably, the formulations should not include oxidizing agents and other substances with which the agents are known to be incompatible. The formulations may conveniently be presented in unit dosage form and may be prepared by any of the methods well known in the art of pharmacy. All methods include the step of bringing into association the agent with the carrier which constitutes one or more accessory ingredients. In general, the formulations are prepared by uniformly and intimately bringing into association the agent with the carrier(s) and then, if necessary, dividing the product into unit dosages thereof.

Formulations suitable for parenteral administration conveniently comprise sterile aqueous preparations of the agents which are preferably isotonic with the blood of the recipient. Suitable such carrier solutions include phosphate buffered saline, saline, water, lactated ringers or dextrose (5% in water). Such formulations may be conveniently prepared by admixing the agent with water to produce a solution or suspension which is filled into a sterile container and sealed against bacterial contamination. Preferably, sterile materials are used under aseptic manufacturing conditions to avoid the need for terminal sterilization.

Such formulations may optionally contain one or more additional ingredients among which may be mentioned preservatives, such as methyl hydroxybenzoate, chlorocresol, metacresol, phenol and benzalkonium chloride. Such materials are of special value when the formulations are presented in multi-dose containers.

Buffers may also be included to provide a suitable pH value for the formulation and suitable materials include sodium phosphate and acetate. Sodium chloride or glycerin may be used to render a formulation isotonic with the blood. If desired, the formulation may be filled into the containers under an inert atmosphere such as nitrogen or may contain an anti-oxidant and are conveniently presented in unit dose or multi-dose form, for example, in a sealed ampoule.

It will be appreciated that while the agents described herein form acid addition salts and carboxyl acid salts, the biological activity thereof will reside in the agent itself. These salts may be used in human and in veterinary medicine and presented as pharmaceutical formulations in the manner and in the amounts (calculated as the base) described hereinabove, and it is then preferable that the acid moiety be pharmacologically and pharmaceutically acceptable to the recipient. Examples of such suitable acids include (a) mineral acids: hydrochloric, hydrobromic, phosphoric, metaphosphoric, and sulfuric acids; (b) organic acids: tartaric, acetic, citric, malic, lactic, fumaric, benzoic, glycollic, gluconic, gulonic, succinic and arylsulfonic, for example, p-toluenesulfonic acids.

In compounds of the invention, $R_1$ and $R_6$ are preferably methyl, ethyl, propyl, benzyl, etc., it being understood that the term "aralkyl" is intended to embrace any aromatic group, the chemical and physical properties of which do not adversely affect the efficacy and safety of the compound for therapeutic applications. Preferred, however, are the hydrocarbyl aralkyl groups, i.e., comprised only of C and H atoms.

$R_2$–$R_5$ preferably are H, methyl, ethyl, propyl or benzyl.

Compounds of the above formulae are synthesized according to the methods described in application Ser. No. 07/210,520 filed Jun. 23, 1988, now U.S. Pat. No. 5,091,576, and Ser. No. 07/870,441 filed Oct. 9, 1991, the entire contents and disclosures of both of which are incorporated herein by reference.

Although, as noted above, it has been reported that diethylhomospermine (DEHSPM) inhibits gastrointestinal motility in rats, it has been determined that this inhibition is extremely dependent on structural motifs within the molecule. Preliminary receptor binding experiments suggest that DEHSPM is not a classic anti-cholinergic or anti-adrenergic.

The invention is illustrated by the following non-limiting examples.

EXAMPLE 1

This study represents an attempt to elucidate a possible mechanism(s) for the above-noted observed inhibition of gastrointestinal motility in rats. The phasic and 20 sustained contractions of guinea pig taenia coli were determined in a perfused organ bath apparatus. DEHSPM (0.1 mM, 0.5 mM and 1.0 mM) progressively inhibited spontaneous phasic contractions by a TTX-insensitive mechanism. TTX (1.0–20.0 µM) blocked field stimulation-induced contractions without altering the DEHSPM attenuation of phasic contractions:

| Treatment | Phasic Contract/20 min. | Amplitude/20 min. |
| --- | --- | --- |
| Baseline | 5.8 ± 0.4 | 4.8 ± 0.3 |
| DEHSPM (1.0 mMm) | 2.3 ± 0.5*** | 2.2 ± 0.4*** |

***$p < 0.0001$ compared to baseline. Data expressed as mean ± SEM.

In an attempt to support the above bethanechol experiments, increasing cumulative concentrations of carbachol (1.0 nM to 1.0 µM half-log changes) were used alone and following DEHSPM (1.0 mM). Only the highest concentration (1.0 µM) of carbachol was able to overcome the inhibitory effects of DEHSPM. Interestingly, the majority of the tissues tested (>80%) were of the phasic contractile type. In order to consistently test the sustained contractions, 20 mM KCl was used to induce a sustained contraction. Similar to the phasic tissues, DEHSPM (1.0 mM) significantly inhibited the KCl-induced contraction. Results are expressed as the extent of relaxation (%) and as compared to nitroprusside (1.0 mM), a classic relaxation agent:

| Treatment | % Relaxation | % Nipride Relaxation |
| --- | --- | --- |
| DEHSPM (1.0 mM) | 81 ± 11 | 240 |
| DEHSPM (0.5 mM) | 33 ± 4 | 129 |
| DEHSPM (0.1 mM) | 5 ± 2 | 16 |

Both the nitric oxide synthase inhibitor, L-NAME (20 µmM), and methylene blue (10 µM) partially blocked the inhibition caused by DEHSPM. Hemoglobin-containing compounds partially block DEHSPM-induced inhibition of phasic contractions and relaxation of KCl-induced contractions. It can be deduced, therefore, from the above results that the profound inhibition caused by DEHSPM in isolated GI tissues is due, in part, to a nitric oxide mechanism. DEHSPM apparently causes relaxation either through a direct myogenic interaction or through an Na-independent neural pathway.

EXAMPLE 2

To test the hypothesis that DEHSPM would cause alterations of myoelectric activity and transit of the small intestine similar to those noted with the use of isoproterchol (ISO), myoelectric activity was monitored in rats during fasting by four in-dwelling electrodes. Intestinal transit was measured by the movement of radiochromium, expressed as the geometric center. Intestinal myoelectric activity and transit were determined after a single s.c. injection of saline or 5 mg/kg DEHSPM. In addition, myoelectric activity was monitored after chronic administration of 5 mg/kg bid for 6 days. The interval between activity fronts (AF) of the migrating myoelectric complex (MMC), propagation velocity of the AF and the duration of spike inhibition (min.) after each injection are reported below:

|  | AF Interval | AF Propagation Velocity | Inhibition | Geo. Ctr. |
| --- | --- | --- | --- | --- |
| Baseline Single | 10.8 ± 1.0 | 3.0 ± 0.5 | — | 4.0 ± 0.5 |
| Day 1 | 22.6 ± 1.6* | 1.3 ± 0.1* | 44.5 ± 3.2* | 1.3 ± 0.2* |
| Day 4 | 14.7 ± 2.4 | 1.5 ± 0.1* | — | — |
| Chronic Day 5 | 40.3 ± 8.9* | 1.8 ± 0.3 | — | — |

Mean ± SEM in minutes. *p 0.05 propagation velocity = cm/min.

In summary, therefore, it can be stated, based on the above evidence, that (1) DEHSPM causes significant inhibition of small intestinal myoelectric activity; (2) DEHSPM significantly delays transit of small intestine; and (3) chronic administration of DEHSPM induces profound alterations of intestinal motility.

These findings with DEHSPM are similar to those reported after administration of ISO, but DEHSPM-induced alterations have a much longer duration. It is hypothesized that polyamines may interact non-covalently with specific biochemical macromolecules or a second messenger system responsible for the maintenance of intestinal motility. Furthermore, the gastrointestinal toxicity observed with DEHSPM appears to be related to alterations of intestinal motility.

EXAMPLE 3

Further studies were conducted to determine the effect of DEHSPM on gastric emptying and selected pharmacologic agents were used to determine the mechanism of action. A radiochromium method was used to measure the % gastric emptying (GE) and intestinal transit expressed as geometric center (GC). Percent GE, % reversal in GE from DEHSPM treatment and GC were determined after a single dose of DEHSPM and the respective pharmacologic agent with the following results:

| Treatment (mg/kg Route) | % GE | % Reversal | GC |
| --- | --- | --- | --- |
| Saline Control | 82.5 ± 3.0 | 100.0 | 5.1 ± 0.3 |
| DEHSPM (5 sc) + Saline | 14.3 ± 4.2 | — | 1.5 ± 0.2 |
| Metoclopramide (5 ip) | 27.4 ± 2.3 | 19.6* | 1.6 ± 0.1 |
| Verapamil (5 ip) | 45.4 ± 2.8 | 45.2*** | 2.3 ± 0.1** |
| Propranolol (5 sc) | 44.7 ± 5.3 | 44.2** | 1.9 ± 0.2 |
| Yohimbine (1 sc) | 31.3 ± 5.7 | 24.4 | 2.1 ± 0.2 |
| Naloxone (1 sc) | 34.4 ± 6.5 | 29.2 | 2.2 ± 0.2 |
| Bethanechol |  |  |  |
| (0.05 ip) | 44.8 ± 8.2 | 44.3** | 2.2 ± 0.1 |
| (0.5 ip) | 85.2 ± 2.8 | 103.0*** | 3.6 ± 0.2*** |
| (10.0 ip) | 94.9 ± 0.9 | 117.2*** | 6.4 ± 0.3*** |

Mean ± SEM. p values: *<0.05, <0.02, *<0.0002

In summary, (1) DEHSPM significantly delayed GE and small intestinal transit; (2) DEHSPM's inhibition of GE was only partially but significantly reversed by dopaminergic, calcium channel, and β-adrenergic antagonists. In contrast, bethanechol completely reversed DEHSPM's effect. (3) DEHSPM's inhibition of intestinal transit was improved significantly by a calcium channel antagonist and a cholinergic agonist.

These data suggest that calcium mobilization and the β-adrenergic system are intimately involved in DEHSPM's effect on motility. This is probably not an atropine-like effect because atropine does not inhibit motility in rats. It can be postulated that bethanechol may provide an important adjunct to chemotherapeutic regimes containing analogs of the polyamine pathway.

EXAMPLE 4

The activity of DEHSPM as a potent anti-diarrheal agent was tested in a castor oil-induced diarrhea model in rats. Fasted rats were injected s.c. with saline or DEHSPM at 0.2, 1.0 or 5.0 mg/kg and had orogastric gavage of 2 ml of castor oil. Time of first diarrheal stool (min.) and weight (wt.) loss at 2, 4 and 6 hours were measured. The results are expressed below as mean ±SEM.

|  | 1st stool | 2 Hour Wt. Loss | 4 Hour Wt. Loss | 6 Hour Wt. Loss |
| --- | --- | --- | --- | --- |
| Saline | 104 ± 30 | 4.1 ± 0.9 | 7.2 ± 1.2 | 9.1 ± 1.1 |
| 0.2 mg/kg | 261 ± 40* | 1.6 ± 0.4* | 3.8 ± 0.6* | 5.2 ± 0.7* |
| 1.0 mg/kg | >360** | 0.7 ± 0.3** | 2.0 ± 0.3** | 2.5 ± 0.4** |
| 5.0 mg/kg | >360** | 1.1 ± 0.3** | 1.9 ± 0.3** | 2.6 ± 0.4** |

*p <0.02 and **p <0.001 compared to saline + castor oil

Interestingly, L-NAME, a nitric oxide synthase inhibitor, is reported to prevent diarrhea in this animal model and it can be reversed with L-arginine. DEHSPM may interact with oxygen radicals because it has potent cyto-protective effects against alcohol-induced gastritis. Therefore, it was hypothesized that L-arginine may reverse DEHSPM's anti-diarrheal effect. L-arginine, 600 mg/kg i.p., failed to alter DEHSPM's beneficial effects in this model. In summary, then, DEHSPM is a potent anti-diarrheal agent that profoundly inhibits motility. The possibility cannot be excluded that DEHSPM may also have anti-secretory activity because the lowest dose that was effective in this diarrheal model has only limited anti-transit effects.

EXAMPLE 5

The mechanism by which DEHSPM inhibits diarrhea was further studied by investigating the effects of the compound on cholera-induced secretion in the ligated intestinal loop model in rats. In this model, the rats were anesthetized and isolated intestinal loops were separated and 10 μg of cholera toxin was injected along with a small amount of saline. DEHSPM caused a significant reduction in the amount of accumulated fluid in jejunal segments and a trend to decrease fluid acceleration in the ileum. This effect was dose-related and occurred at 0.2 mg/kg s.c., but its enhanced absorption was more marked at the 1 and 5 mg/kg dose. The results from those doses compared favorably to the response observed with large doses of clonidine, in $\alpha_2$-adrenergic agonist used in reference compound.

We claim:

1. An anti-diarrheal or gastrointestinal anti-spasmodic pharmaceutical composition comprising an effective amount of a compound having the formula:

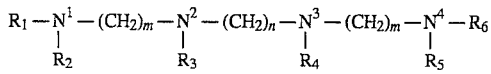 (I)

or

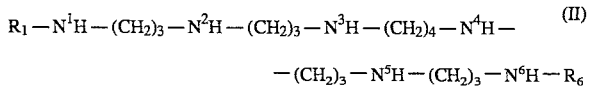 (II)

wherein:

R$_1$–R$_6$ may be the same or different and are alkyl of 1–5 carbon atoms or hydrocarbyl aralkyl up to 12 carbon atoms;

m is an integer from 3 to 6, inclusive; and n is an integer from 3 to 6, inclusive; or a salt thereof with a pharmaceutically acceptable acid; and a pharmaceutically acceptable carrier therefor.

2. A composition according to claim 1 wherein R$_1$ and R$_6$ are t-butyl.

3. A composition according to claim 1 wherein said compound has the formula (I) and m is 3 and n is 4.

4. A composition according to claim 1 wherein said compound has the formula (I) and m is 3 and n is 3.

5. A composition according to claim 1 wherein said compound has the formula (I) and m is 4 and n is 4.

6. A method of treating diarrhea or gastrointestinal spasm in a human or non-human animal in need thereof comprising administering to said animal an effective amount of a compound having the formula:

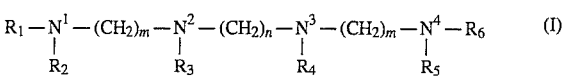 (I)

or

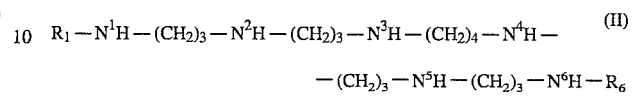 (II)

wherein:

R$_1$–R$_6$ may be the same or different and are alkyl of 1–5 carbon atom or aralkyl up 12 carbon atoms;

m is an integer from 3 to 6, inclusive; and n is an integer from 3 to 6, inclusive; or a salt thereof with a pharmaceutically acceptable acid.

7. A method according to claim 6 wherein R$_1$ and R$_6$ are t-butyl.

8. A method according to claim 6 wherein said compound is of formula (I) and wherein m is 3 and n is 4.

9. A method according to claim 6 wherein said compound is of formula (I) and wherein m is 3 and n is 3.

10. A method according to claim 6 wherein said compound is of formula (I) and wherein m is 4 and n is 4.

* * * * *

UNITED STATES PATENT AND TRADEMARK OFFICE
CERTIFICATE OF CORRECTION

PATENT NO. : 5,462,970
DATED      : Oct. 31, 1995
INVENTOR(S) : Raymond J. Bergeron, Jr.
              Charles A. Sninsky It is certified that error appears in the above-indentified patent and that said Letters Patent is hereby corrected as shown below:

<u>Claim 6, line 13, (Column 10, line 16):</u>

Change "atom" to "atoms";

After "or", insert -- hydrocarbyl --;

After "up", insert -- to --.

Signed and Sealed this

Twentieth Day of February, 1996

Attest:

BRUCE LEHMAN

*Attesting Officer*    *Commissioner of Patents and Trademarks*